United States Patent

Sakuta et al.

Patent Number: 5,973,066
Date of Patent: Oct. 26, 1999

[54] OIL-IN-WATER AQUEOUS ORGANOPOLYSILOXANE EMULSION AND METHOD FOR THE PREPARATION THEREOF

[75] Inventors: Koji Sakuta; Morizo Nakazato; Teruki Ikeda, all of Gunma-ken, Japan

[73] Assignee: Shin-Etsu Chemical Co., Ltd., Tokyo, Japan

[21] Appl. No.: 09/192,581

[22] Filed: Nov. 17, 1998

[30] Foreign Application Priority Data

Nov. 17, 1997 [JP] Japan .................................... 9-315087
Nov. 17, 1997 [JP] Japan .................................... 9-315096

[51] Int. Cl.$^6$ ............................................. B01J 13/00
[52] U.S. Cl. ............................ 524/837; 516/55; 516/67; 516/72
[58] Field of Search ............................. 524/837; 516/55, 516/67, 72

[56] References Cited

U.S. PATENT DOCUMENTS

| 3,208,911 | 9/1965 | Oppliger ................................. 167/87 |
| 5,286,476 | 2/1994 | Nanba et al. ............................ 424/47 |
| 5,482,703 | 1/1996 | Pings ..................................... 424/70.12 |
| 5,788,884 | 8/1998 | Kuwata et al. ......................... 252/312 |

FOREIGN PATENT DOCUMENTS 0 798 332   10/1997   European Pat. Off. .

OTHER PUBLICATIONS

Patent Abstracts of Japan, vol. 95, No. 010, Nov. 30, 1995; Pub. No. 07188557.

*Primary Examiner*—Margaret G. Moore
*Attorney, Agent, or Firm*—Millen, White, Zelano & Branigan, P.C.

[57] ABSTRACT

An oil-in-water aqueous organopolysiloxane emulsion suitable as an adjuvant, in particular, in a toiletry preparation such as a hair-care treatment preparation is disclosed by using a unique emulsification system including a quaternary ammonium chloride as a cationic surface active agent, in order to provide a solution for the problem of a dilemma between the use of a $C_{16}$ or lower-alkyl quaternary ammonium salt having high emulsification power but exhibiting irritativeness to the human body and the use of a higher-alkyl quaternary ammonium salt having lower emulsification power but exhibiting no irritativeness. The emulsion composition comprises: (A) a high-polymeric organopolysiloxane mixed with and diluted by an organopolysiloxane of a lower viscosity; (B) a quaternary ammonium chloride having 1 or 2 stearyl or behenyl groups; (C) a polyoxyalkylene-modified organopolysiloxane or a polyhydric alcohol as an activity-promoting agent for the component (B); and (D) water each in a specified weight proportion. The emulsion can be prepared by first forming a water-in-oil emulsion from the respective ingredients though with a reduced amount of water, then effecting phase inversion of the emulsion by continued agitation from the water-in-oil emulsion to an oil-in-water emulsion; and diluting the emulsion with an additional amount of water.

21 Claims, No Drawings

OIL-IN-WATER AQUEOUS ORGANOPOLYSILOXANE EMULSION AND METHOD FOR THE PREPARATION THEREOF

BACKGROUND OF THE INVENTION

The present invention relates to an aqueous emulsion of a high-polymeric organopolysiloxane of the oil-in-water type having excellent stability of emulsion or, more particularly, to an oil-in-water aqueous emulsion of an organopolysiloxane suitable for use as an adjuvant in various kinds of toiletry and cosmetic preparations and for use in other applications.

It is a well established technology that an aqueous emulsion of an organopolysiloxane is used as an additive ingredient in a wide variety of compositions including toiletry and cosmetic preparations, polishing agents, mold-release agents, fabric-finishing agents and others. In particular, hair-care treatment toiletry preparations are, in many cases, formulated with such an organopolysiloxane emulsion as an adjuvant of which the organopolysiloxane contained in the aqueous emulsion should have an average degree of polymerization or viscosity as high as possible because the adherence of the organopolysiloxane to the surface of the hair treated with the hair-care treatment preparation can be improved as the average degree of polymerization of the organopolysiloxane is increased as compared with an organopolysiloxane of a low degree of polymerization or low viscosity.

For example, Japanese Patent Kokai 4-36226 and 4-224309 propose a formulation of a shampoo composition with admixture of an aqueous emulsion of a high-polymeric organopolysiloxane. According to the disclosures therein, the foamability of the shampoo composition is never or little affected when the organopolysiloxane droplets as the dispersed phase in the aqueous emulsion added thereto have a particle diameter not exceeding 2 µm. Further, Japanese Patent Kokai 63-130521, 5-13994 and 5-163122 teach a method in which an organopolysiloxane is used as an adjuvant of various base compositions in the form of a so-called microemulsion.

Though excellent in the stability of the aqueous emulsion and high foamability of the toiletry preparations, the above mentioned current toward the use of an aqueous organopolysiloxane emulsion having a small particle diameter of the organopolysiloxane droplets dispersed therein has a problem that, when the toiletry preparation is a hair-care treatment preparation, adherence of the organopolysiloxane to the surface of the hair treated therewith is not good enough so that the advantageous effects desired for the hair treatment is readily lost by rinse. As is taught in Japanese Patent Kokai 7-188557, this problem can be solved by the use of an aqueous organopolysiloxane emulsion of which the organopolysiloxane droplets have a relatively large particle diameter in the range from 3 to 100 µm. Though suitable as an adjuvant in shampoo compositions, the aqueous organopolysiloxane emulsion disclosed there, however, has a problem that, when the emulsion is admixed with a hair-care treatment preparation, such as rinses, hair conditioners and treatments, which are sometimes formulated with a cationic surface active agent while the emulsion disclosed there is prepared by using an anionic surface active agent as the emulsifying agent, the incompatibility of the different surface active agents results in phase separation or precipitation of the ingredients so that a hair-care treatment preparation having excellent stability cannot be obtained.

With an object to solve the above mentioned problem of instability of emulsions, a proposal has been made by the inventors for the use of a cationic surface active agent as an emulsifying agent in the preparation of an aqueous organopolysiloxane emulsion. According to this proposal, the cationic surface active agent is a salt having a quaternary ammonium group in the molecule. While it is known that the stability of the aqueous organopolysiloxane emulsion prepared by using a quaternary ammonium salt as the cationic emulsifying agent can be high when the alkyl group or groups forming the quaternary ammonium group have a small number of carbon atoms to give an increased surface activity, such a lower alkyl-containing quaternary ammonium salt has an antimicrobial activity on the other side, which means that the compound is strongly irritative against human skins, mucous membranes and eyes not to be suitable as an ingredient in a toiletry preparation. This disadvantage of irritativeness against human body can at least partly be overcome by the use of a quaternary ammonium salt having at least one long-chain alkyl group with 18 or more carbon atoms. Although the adverse effect on the foamability caused by the use of a long-chain alkyl-containing quaternary ammonium salt is not so detrimental if the long-chain alkyl group has 16 carbon atoms or less, the organopolysiloxane droplets in the aqueous emulsion cannot have a particle diameter fine enough to greatly decrease the stability of the emulsion when the long-chain alkyl group in the quaternary ammonium salt has 18 carbon atoms or more.

SUMMARY OF THE INVENTION

The present invention accordingly has an object to provide, by overcoming the above mentioned dilemma in the use of a long-chain alkyl-containing quaternary ammonium salt as the cationic surface active agent, to provide an oil-in-water aqueous emulsion of a high-polymeric organopolysiloxane having good storage stability of the emulsion and suitable for use as an adjuvant, for example, in toiletry or cosmetic preparations.

Thus, the oil-in-water aqueous organopolysiloxane emulsion composition provided by the invention comprises, in the form of a uniform emulsion:

(A) 100 parts by weight of an organopolysiloxane mixture having a viscosity of at least 10,000 mm²/s at 25° C. and consisting of (A1) from 10 to 90% by weight of a first organopolysiloxane represented by the average unit formula

$$R^1_a SiO_{(4-a)/2}, \qquad (I)$$

in which $R^1$ is a monovalent hydrocarbon group having 1 to 20 carbon atoms and the subscript a is a positive number in the range from 1.8 to 2.2, and having a viscosity of at least 1,000,000 mm²/s at 25° C., and (A2) from 90 to 10% by weight of a second organopolysiloxane represented by the average unit formula

$$R^2_b SiO_{(4-b)/2}, \qquad (II)$$

in which $R^2$ is a monovalent hydrocarbon group having 1 to 20 carbon atoms and the subscript b is a positive number in the range from 1.8 to 2.2, and having a viscosity in the range from 2 to 1000 mm²/s at 25° C. or a liquid hydrocarbon compound having a boiling point under normal pressure in the range from 60 to 200° C.;

(B) from 0.5 to 20 parts by weight of a cationic surface active agent which is a quaternary ammonium halide represented by the general formula $$[R^3{}_n R^4{}_{4-n} N]^+ X^-, \quad (III)$$

in which $R^3$ is an alkyl or alkenyl group having 18 or 22 carbon atoms, $R^4$ is an alkyl group having 1 to 5 carbon atoms or a benzyl group, $X^-$ is a halogen ion and the subscript n is a positive integer not exceeding 4 or, preferably, 1 or 2, the amount being preferably at least 1 part by weight when $R^3$ has 22 carbon atoms;

(C) from 0.05 to 20 parts by weight of an activity promoting agent selected from the group consisting of (C1) when the group $R^3$ in the component (B) has 18 carbon atoms, polyoxyalkylene-modified organopolysiloxanes represented by the average unit formula $$R^5{}_c R^6{}_d SiO_{(4-c-d)/2}, \quad (IV)$$

in which $R^5$ is an unsubstituted or substituted monovalent hydrocarbon group having 1 to 20 carbon atoms, $R^6$ is a monovalent polyoxyalkylene-substituted alkyl group represented by the general formula $$-(C_e H_{2e}) O (C_2 H_4 O)_f (C_3 H_6 O)_g R^7, \quad (V)$$

$R^7$ being a hydrogen atom or an alkyl or acyl group having 1 to 20 carbon atoms, the subscript e being a positive integer in the range from 2 to 15, the subscript f being a positive integer in the range from 3 to 200 and the subscript g being 0 or a positive integer not exceeding 100, the subscript c is a number in the range from 1.0 to 2.5 and the subscript d is a number in the range from 0.005 to 1.2 with the proviso that c+d is in the range from 1.8 to 3.0, and (C2) when the group $R^3$ in the component (B) has 22 carbon atoms, polyhydric alcohols, the amount of the component (C) being at least 1 part by weight when the activity promoting agent is a polyhydric alcohol; and (D) from 10 to 300 parts by weight of water, of which the droplets as the dispersed phase preferably have an average diameter in the range from 1 to 20 μm.

The above defined oil-in-water aqueous organopolysiloxane emulsion composition can be prepared by a method which comprises the steps of:

(a) agitating a mixture consisting of 100 parts by weight of the component (A), from 0.5 to 20 parts by weight of the component (B), from 0.05 to 20 parts by weight of the component (C) and from 0.5 to 20 parts by weight of water to form a water-in-oil emulsion;

(b) agitating the water-in-oil emulsion to effect phase inversion of the water-in-oil emulsion into an oil-in-water emulsion; and (c) diluting the oil-in-water emulsion obtained in step (b) with addition of an additional amount of water sufficient to make up a total amount of water not to exceed 300 parts by weight.

DETAILED DESCRIPTION OF THE PREFERRED EMBODIMENTS

As is described above, the high-polymeric first organopolysiloxane as the principal ingredient, i.e. component (A1), in the inventive aqueous emulsion, which is introduced into the aqueous emulsion in the form of an organopolysiloxane mixture as the component (A), is represented by the average unit formula (I) given above, in which the subscript a has a value in the range from 1.8 to 2.2. In this formula, the group denoted by $R^1$ is a monovalent hydrocarbon group having 1 to 20 carbon atoms, which can optionally be substituted by some substituent atoms or groups, exemplified by alkyl groups such as methyl, ethyl, propyl, butyl, pentyl, hexyl, heptyl, octyl, nonyl, decyl, dodecyl, tetradecyl, hexadecyl and octadecyl groups, aryl groups such as phenyl and tolyl groups, cycloalkyl groups such as cyclopentyl and cyclohexyl groups, fluorine-substituted alkyl groups such as 3,3,3-trifluoropropyl, 2-(perfluorobutyl)ethyl and 2-(perfluorooctyl)ethyl groups and amino-substituted alkyl groups such as 3-aminopropyl and 3-(N-2-aminoethylamino)propyl groups as well as monovalent hydrocarbon groups substituted by epoxy groups, mercapto groups, (meth)acryloxy groups, acyloxyalkyl groups, carboxyl groups, hydroxyl groups and the like, of which methyl, phenyl and amino-substituted alkyl groups are preferable. In particular, it is most preferable that at least 50% or at least 90% by moles of the groups denoted by $R^1$ are methyl groups.

As is mentioned before, it is a desirable condition that the high-polymeric organopolysiloxane as the principal ingredient in the aqueous organopolysiloxane emulsion has an average degree of polymerization or viscosity as high as possible, when the emulsion is used as an adjuvant in a hair-care treatment preparation, in order to improve adherence of the organopolysiloxane to the hair. In this regard, the high-polymeric first organopolysiloxane as the component (A1) preferably has a viscosity of at least 1,000,000 mm²/s or, more preferably, at least 10,000,000 mm²/s at 25° C.

The second organopolysiloxane as the component (A2), which is combined with the first organopolysiloxane as the component (A1) to form an organopolysiloxane mixture as the component (A), is a so-called silicone oil and represented by the average unit formula (II) given above, in which the subscript b has a value in the range from 1.8 to 2.2 and the group denoted by $R^2$ is an unsubstituted or substituted monovalent hydrocarbon group having 1 to 20 carbon atoms and exemplified by the same groups named above as the examples of the group $R^1$ in the first organopolysiloxane.

Since this second organopolysiloxane serves as a diluent of the high-polymeric organopolysiloxane to facilitate emulsification thereof, it is preferable that the second organopolysiloxane has a viscosity in the range from 2 to 1000 mm²/s or, more preferably, from 10 to 500 mm²/s at 25° C. An organopolysiloxane of which the viscosity is too low is undesirable as an ingredient in a toiletry or cosmetic preparation due to the irritativeness against human skin and eyes. When the viscosity of the second organopolysiloxane is too high, on the other hand, the miscibility thereof with the high-polymeric first organopolysiloxane is decreased not to serve as a diluent of the first organopolysiloxane. Provided that the silicone oil as the component (A2) has a viscosity in the above mentioned range, the molecular structure of the organopolysiloxane is not limited to linear but can be branched or cyclic.

Examples of the cyclic organopolysiloxane having the above mentioned preferable viscosity as the component (A2) include hexamethyl cyclotrisiloxane, octamethyl cyclotetrasiloxane, decamethyl cyclopentasiloxane, dodecamethyl cyclohexasiloxane, 1,3,5-tri(3,3,3-trifluoropropyl)-1,3,5-trimethyl cyclotrisiloxane, 1,3,5,7-tetra(3,3,3-trifluoropropyl)-1,3,5,7-tetramethyl cyclotetrasiloxane and 1,3,5,7,9-penta-(3,3,3-trifluoropropyl)-1,3,5,7,9-pentamethyl cyclopentasiloxane, of which octamethyl cyclotetrasiloxane is preferable.

Alternatively, the component (A2) to serve as a diluent of the high-polymeric first organopolysiloxane as the component (A1) can be a liquid hydrocarbon compound having a boiling point in the range from 60 to 260° C. under normal pressure. A hydrocarbon compound having a boiling point lower than 60° C. is undesirable as an ingredient of, in particular, toiletry or cosmetic preparations due to the unpleasant odor while a liquid hydrocarbon compound having a boiling point higher than 260° C. is less effective as a diluent of the high-polymeric organopolysiloxane as the component (A1).

Examples of the liquid hydrocarbon compound suitable as the component (A2) include various kinds of commercially available hydrocarbon solvents sold under the trade names of Isopars C, E, G, H, L and M (each a product by Exxon Co.), IP Solvents 1016, 1620 and 2028 (each a product by Idemitsu Petrochemical Co.), Marucasol R (a product by Maruzen Petrochemical Co.), Nisseki Isols 300 and 400 (each a product by Nippon Petrochemical Co.), Shellsol 71 (a product by Shell Chemical Co.), Solutols 100, 130 and 220 (each a product by Phillips Co.) and Isohexadecane (a product by Baeyer Japan Co.), though not particularly limitative thereto.

The blending proportion of the component (A1) and the component (A2) described above to form the component (A) can be in the range from 90:10 to 10:90 by weight. It is preferable, however, that the blending proportion thereof is selected such that the component (A) as a mixture of the components (A1) and (A2) has a viscosity of at least 10,000 $mm^2/s$ at 25° C. When the viscosity of the mixture is too low, the mixture is deficient in the content of the high-polymeric organopolysiloxane as the component (A1) so that, for example, a hair-care treatment toiletry preparation compounded with the aqueous emulsion is less effective in imparting a pleasant touch feeling to the hair treated therewith due to a decrease in the adherence of the organopolysiloxane ingredient to the hair. When the component (A1) is a high-polymeric dimethyl polysiloxane and the component (A2) is a low-polymeric dimethyl polysiloxane, in particular, it is more preferable that the weight proportion of the component (A1) is increased such that the component (A) as a mixture thereof has a viscosity of at least 100,000 $mm^2/s$ at 250° C.

The component (B) in the inventive aqueous emulsion is a quaternary ammonium salt which serves as a cationic surface active agent. The quaternary ammonium salt is represented by the general formula (III) given before, in which $R^3$ is a long-chain alkyl or alkenyl group having at least 18 or, preferably, 18 or 22 carbon atoms, $R^4$ is a benzyl group or an alkyl group having 1 to 5 carbon atoms or, preferably, methyl group, $X^-$ is an anion of a halogen or, preferably, chlorine and the subscript n is a positive integer not exceeding 4 or, preferably, 1 or 2.

The reason for the selection of the long-chain group denoted by $R^3$ from those having at least 18 carbon atoms is that, although quarternary ammonium salt compounds may exhibit surface activity when the molecule has at least one alkyl or alkenyl group having 12 or more carbon atoms, the quaternary ammonium salt compounds of which the long-chaim group has 16 or less carbon atoms have irritativeness against human skins and rather are toxic so that an aqueous emulsion formulated with such a surface active agent cannot be used in a toiletry preparation. For example, lauryl trimethyl ammonium chloride can be used as a bactericidal agent or antiseptic agent. Hexadecyl trimethyl ammonium chloride has an $LD_{50}$ value of 250 to 300 mg/kg (rat) while the $LD_{50}$ value of stearyl trimethyl ammonium chloride is 1000 mg/kg (rat) and the $LD_{50}$ value of behenyl trimethyl ammonium chloride is still higher. The reason for the preference of the quaternary ammonium salt compounds of which the long-chain alkyl or alkenyl group has 18 or 22 carbon atoms is that the quaternary ammonium compounds of which the long-chain group has 19–21 or 23 or more carbon atoms are industrially less available. The $C_{22}$ quaternary ammonium salt compounds are preferable to the $C_{18}$ compounds from the standpoint of safety.

Particular examples of the quaternary ammonium salt compound suitable as the component (B) in the inventive aqueous emulsion include stearyl trimethyl ammonium chloride, distearyl dimethyl ammonium chloride, stearyl dimethyl benzyl ammonium chloride, dioleyl dimetyl ammonium chloride, behenyl trimethyl ammonium chloride, dibehenyl dimethyl ammonium chloride and dibehenyl methyl benzyl ammonium chloride, of which stearyl trimethyl ammonium chloride and behenyl trimethyl ammonium chloride are preferable, though not particularly limitative thereto. It was noted that a quaternary ammonium salt compound of which the long-chain group has 22 carbon atoms is less compatible with the polyoxyalkylene-modified organopolysiloxane as a class of the component (C) described later.

The amount of the quaternary ammonium salt compound as the component (B) in the inventive aqueous emulsion is in the range from 0.5 to 20 parts by weight per 100 parts by weight of the component (A). When the quaternary ammonium salt compound is a $C_{22}$ compound, the amount is preferably in the range from 1 to 20 parts by weight per 100 parts by weight of the component (A). When the amount of the surface active agent as the component (B) is too small, a stable aqueous emulsion cannot be obtained as a matter of course. When the amount of the component (B) is too large, the human skin or hair after treatment with a toiletry preparation containing the aqueous organopolysiloxane emulsion may exhibit some stickiness not to give a pleasant touch feeling. When the quaternary ammonium salt compound is obtained in the form of an aqueous solution containing, for example, 10 to 50% by weight of the compound, the aqueous solution can be used as such in the preparation of the inventive aqueous emulsion.

The component (C) is an activity-promoting agent which is selected from two classes of compounds including (C1) polyoxyalkylene-modified organopolysiloxanes and (C2) polyhydric alcohols, of which the polyhydric alcohols are preferable when the quaternary ammonium salt compound as the component (B) is a compound having at least one $C_{22}$ long-chain alkyl or alkenyl group in the molecule. The component (C) is an essential ingredient in order for the aqueous organopolysiloxane emulsion to have a particle size of the dispersed liquid droplets in the range from 1 to 20 or, preferably, from 2 to 20 $\mu$m. When the aqueous emulsion is prepared by using the component (B) alone without the component (C), the dispersed liquid droplets cannot be so fine that the stability of the emulsion is greatly decreased.

The polyoxyalkylene-modified organopolysiloxane as the first class of the component (C) is represented by the average unit formula (IV) given before, in which $R^5$ is a monovalent hydrocarbon group having 1 to 20 carbon atoms, $R^6$ is a monovalent polyoxyalkylene-substituted alkyl group represented by the general formula (V) given before, the subscript c is a number in the range from 1.0 to 2.5 or, preferably, from 1.2 to 2.3 and the subscript d is a number in the range from 0.005 to 1.2 or, preferably, from 0.01 to 1.0 with the provise that c+d is in the range 1.8 to 3.0. When the subscript c is too small or the subscript d is too large, the organopolysiloxane is deficient in the content of the groups $R^5$ so that the miscibility or dispersibility thereof with the organopolysiloxane mixture as the component (A) is decreased not to fully serve as an activity-promoting agent. When the subscript c is too large or the subscript d is too small, the activity-promoting effect thereof is also decreased due to the deficiency in the content of the hydrophilic polyoxyalkylene groups.

In the general formula (V) representing the polyoxyalkylene-substituted alkyl group $R^6$, the subscript e is a positive integer in the range from 2 to 15 or, preferably, from 3 to 12, the subscript f is an average number in the range from 3 to 200 or, preferably, from 5 to 100 and the subscript g is 0 or an average number not exceeding 100 or, preferably, an average number in the range from 1 to 100 in order that the polyoxyalkylene-modified organopolysiloxane may have good solubility in water.

It is preferable that the polyoxyalkylene-modified organopolysiloxane as the component (C1) has an average molecular weight not exceeding 3000 because, when the molecular weight thereof is too large, good miscibility or dispersibility cannot be obtained between the polyoxyalkylene-modified organopolysiloxane and the organopolysiloxane mixture as the component (A). It is further preferable that the polyoxyalkylene-modified organopolysiloxane as the component (C1) has an HLB value of 7 or larger and a 0.1% by weight aqueous solution thereof has a surface tension not exceeding 30 dyn/cm at 25° C.

It would be an alternative idea, in place of the above described polyoxyalkylene-modified organopolysiloxane, to use another water-soluble modified organopolysiloxane having hydrophilic substituent groups as the component (C1). When a silicone compound having an anionic group such as sulfate ester groups is used, for example, the silicone compound may form a complex with the cationic surface active agent as the component (B) not to exhibit good surface activity required for emulsification of the component (A). When a silicone compound modified with quaternary ammonium groups is used as the component (C1), good hydrophilicity of the compound can be obtained only with a high degree of modification so that a toiletry preparation such as a hair-care treatment preparation containing such a silicone compound is defective due to the stickiness imparted to the hair treated therewith. A similar disadvantage is encountered in the use of a silicone compound modified with glyceryl or polyglyceryl groups as the component (C1).

The activity-promoting agent, i.e. component (C), of the other class (C2) is a polyhydric alcohol which is preferable to the class (C1) compounds, in particular, when the quaternary ammonium salt compound as the component (B) has a long-chain alkyl or alkenyl group having 22 carbon atoms. Examples of the polyhydric alcohol suitable as the component (C2) include ethyleneglycol, propyleneglycol, diethyleneglycol, 1,3-butyleneglycol, 1,4-butyleneglycol, glycerin, diglycerin, triglycerin and trimethylol propane, of which glycerin and 1,3-butyleneglycol are preferable, though not particularly limitative thereto.

The amount of the component (C) in the inventive aqueous organopolysiloxane emulsion is selected in the range from 0.05 to 20 parts by weight per 100 parts by weight of the organopolysiloxane mixture as the component (A) depending on the types of the component (C) which may be the component (C1) or component (C2). When the component (C) is a polyoxyalkylene-modified organopolysiloxane as the component (C1), namely, the amount can be relatively small in the range from 0.05 to 5 parts by weight per 100 parts by weight of the component (A) while, when the component (C) is a polyhydric alcohol, i.e. component (C2), the amount should be relatively large in the range from 1 to 20 parts by weight per 100 parts by weight of the component (A). It is optional that a part of the polyhydric alcohol as the component (C2) is replaced with the polyoxyalkylene-modified organopolysiloxane as the component (C1). The amount of replacement here, however, should not exceed 5 parts by weight per 100 parts by weight of the component (A).

The component (D) in the inventive aqueous emulsion is water which serves as a dispersion medium of the other ingredients. The amount of water is in the range from 10 to 300 parts by weight or, preferably, from 20 to 100 parts by weight per 100 parts by weight of the component (A). When the amount of water is too small, the aqueous emulsion has an excessively high viscosity to cause inconvenience in handling, if not to mention the difficulty encountered in the preparation of the emulsion, while, when the amount of water is too large, a decrease is caused in the stability of the aqueous emulsion.

The above described oil-in-water aqueous organopolysiloxane emulsion is prepared in a two-stage emulsification process. As a typical example, a formulation of the emulsion is assumed to consist of a component (A) which is a 20:80 to 80:20 by weight mixture of a high-polymeric dimethyl polysiloxane having a viscosity of at least 10,000,000 mm$^2$/s at 25° C. as the component (A1) and a dimethyl polysiloxane oil having a viscosity of 20 to 500 mm$^2$/s at 25° C. as the component (A2) and has a viscosity of at least 100,000 mm$^2$/s at 25° C., a component (B) which is a quaternary ammonium chloride, a component (C) which is a polyoxyalkylene-modified organopolysiloxane or a polyhydric alcohol and water as the component (D). Thus, the components (A), (B), (C) and (D) are taken in a weight proportion of 100: (0.05–10): (1–10): (0.5–20) and they are blended and agitated, in the first-stage emulsification, by using a suitable stirrer machine to give a water-in-oil emulsion which is further vigorously agitated, in the second-stage emulsification, to effect phase inversion of the emulsion from the water-in-oil emulsion to an oil-in-water emulsion which is then diluted with addition of an additional amount of water. It is of course that the amount of water taken in the starting mixture is substantially smaller than the overall target amount of water in the finished oil-in-water emulsion. It is optional that, in place of water added for dilution, the oil-in-water emulsion obtained by the phase inversion of the emulsion is diluted with an aqueous solution of the component (B) provided that the overall amount of the component (B) does not exceed the specified upper limit of the amount thereof in the inventive oil-in-water emulsion.

The stirrer machine used in the emulsification of the above described various ingredients to prepare the inventive emulsion is not particularly limitative if the machine is so powerful as to effect phase inversion of the emulsion with a high shearing force. Various commercially available stirrer machines are suitable for the purpose. Examples of suitable machines include those sold under the trade names of Ultramixers, Planetary Mixers, Combi-Mixers, Pipeline Homo-mixers, Homomic Line Mills and Filmics. When the agitatation treatment in the second stage after the phase inversion is terminated too early, the particle size distribution is somewhat broader resulting in a decrease in the stability of the emulsion. When the agitation treatment after the phase inversion is continued too long, on the other hand, the dispersed droplets are further broken down resulting in the separation of the oily phase from the aqueous phase not to give a stable emulsion. In this regard, the agitating time after the phase inversion is preferably in the range from 20 minutes to 3 hours before dilution.

When the oil-in-water aqueous organopolysiloxane emulsion is prepared according to the above described procedure, the organopolysiloxane droplets dispersed in the aqueous medium have a diameter, usually, in the range from 1 to 20 μm or, in most cases, from 2 to 15 μm although the particle diameter would be somewhat coarser to be in the range, usually, from 2 to 20 μm and, in most cases, from 5 to 15 μm when the component (B) is a $C_{18}$ quaternary ammonium salt compound and the component (C) is a polyoxyalkylene-modified organopolysiloxane. When the diameter of the organopolysiloxane droplets is too small, a hair-care treatment preparation formulated with the emulsion would suffer a decrease in the adherence of the effective ingredients to the hair treated therewith. When the dispersed droplets are too coarse, on the other hand, a decrease is caused in the stability of the toiletry preparation formulated with the aqueous emulsion.

It is of course that the organopolysiloxane mixture as the component (A) used in the invention can be emulsified to give a similar oil-in-water aqueous emulsion by the use of a non-ionic surface active agent which is typically a polyoxyethylene alkyl ether in the first stage emulsification to give a water-in-oil emulsion followed by phase inversion and dilution with water containing or not containing a cationic surface active agent which is typically a quaternary ammonium salt used as the component (B) in the invention to give an oil-in-water emulsion. It is found, however, that an aqueous emulsion by this alternative emulsification method is inferior as an additive in a hair-care treatment toiletry preparation as compared with the aqueous emulsion prepared according to the invention in respect of low adherence of the effective ingredients onto the hair treated with the toiletry preparation. Therefore, use of a non-ionic surface active agent should be avoided in the preparation of the aqueous organopolysiloxane emulsion excepting for the polyoxyalkylene-modified organopolysiloxane or the polyhydric alcohol as the component (C) which may exhibit non-ionic surface activity. Betain-based cationic surface active agents and anionic surface active agents are also undesirable.

It is optional, however, that the aqueous organopolysiloxane emulsion of the invention is admixed with various kinds of other known additives including thickening agents, preservatives, perfumes, dyes, pigments and others each in a limited amount according to need. It is further optional that the aqueous emulsion is admixed with a lower alcohol such as ethyl alcohol, isopropyl alcohol, n-butyl alcohol and the like in an amount not exceeding 10% by weight with an object to prevent loss of flowability or pastiness under a low temperature condition due to an undue increase in the viscosity.

In the following, the oil-in-water aqueous organopolysiloxane emulsion of the invention and the method for the preparation thereof are illustrated in more detail by way of Examples, in which the term of "parts" always refers to "parts by weight" and the values of the viscosity are all those obtained by the measurement at 25° C. In the following Examples and Comparative Examples, organopolysiloxane mixtures, referred to as the Mixtures 1 to 4 hereinafter, described below were used as the component (A).

Mixture 1: A uniform mixture having a viscosity of 800,000 mm²/s prepared by dissolving 40 parts of a high-polymeric dimethyl polysiloxane having a viscosity of 20,000,000 mm²/s in 60 parts of a dimethyl polysiloxane oil having a viscosity of 20 mm²/s Mixture 2: A uniform mixture having a viscosity of 1,000,000 mm²/s prepared by dissolving 50 parts of a high-polymeric methyl phenyl polysiloxane having a viscosity of 15,000,000 mm²/s, of which the content of the phenyl groups was 5% by moles based on overall organic groups, in 50 parts of a dimethyl polysiloxane oil having a viscosity of 200 mm²/s Mixture 3: A uniform mixture having a viscosity of 20,000 mm²/s prepared by dissolving 20 parts of a 3-aminopropyl group-containing high-polymeric dimethyl polysiloxane having a viscosity of 30,000,000 mm²/s, of which the amine equivalent was 700,000 g/mole, in 80 parts of a dimethyl polysiloxane oil having a viscosity of 10 mm²/s Mixture 4: A uniform mixture having a viscosity of 10,000 mm²/s prepared by dissolving 20 parts of a high-polymeric dimethyl polysiloxane having a viscosity of 10,000,000 mm²/s in 80 parts of decamethyl cyclopentasiloxane having a viscosity of 4.0 mm²/s In some of the following Examples and Comparative Examples, five kinds of polyoxyalkylene-modified organopolysiloxanes, referred to as PESx-1 to PESx-5 hereinafter, were used as the component (C1) characterized b the molecular weight and the HLB value as well as by the values of the subscripts m, n, p, q and r and the terminal group R in the general structural formula given below, in which Me is a methyl group, EnO is an oxyethylene group —$(C_2H_4O)$— and PnO is an oxytrimethylene group —$(C_3H_6O)$—:

$Me_3Si$—O—[—$SiMe_2$—O—]$_m$—[—$SiMe(C_pH_{2p}$—O— $EnO_q$—$PnO_r$—R)—O—]$_n$—$SiMe_3$, as tabulated in Table 1 below. A 0.1% by weight aqueous solution of these polyoxyalkylene-modified organopolysiloxanes PESx-1, -2, -3, -4 and -5 had a surface tension of 20.6, 24.0, 26.5, 28.0 and 32.0 dyn/cm, respectively, at 25° C.

TABLE 1

|  | PESx-1 | PESx-2 | PESx-3 | PESx-4 | PESx-5 |
|---|---|---|---|---|---|
| m | 0 | 4 | 2 | 10 | 10 |
| n | 1 | 2 | 4 | 5 | 5 |
| p | 3 | 3 | 11 | 3 | 3 |
| q | 6 | 10 | 8 | 10 | 20 |
| r | 0 | 0 | 0 | 2 | 0 |
| R | $CH_3$ | H | H | $C_4H_9$ | H |
| molecular weight | 558 | 1574 | 2638 | 4552 | 5892 |
| HLB | 9.5 | 11.2 | 10.7 | 9.7 | 14.9 |

The emulsifier machine used in the preparation of the aqueous emulsions described below was a stainless steel dual emulsifier of 5 liters capacity (Model TK Combi-Mix M, manufactured by Tokushu Kika Kogyo Co.) having a high-shearing load unit equipped with an anchor-blade stirrer to agitate the whole volume of the liquid in the vessel and a disk stirrer having oppositely facing upper and lower disks each provided with teeth alternately directed downwardly and upwardly, respectively, along the peripheries of the respective disks.

Further, each of the aqueous emulsions prepared as described below was evaluated for the stability of the emulsion in the following testing procedure. Thus, a 100 g portion of the emulsion was taken in a glass bottle and kept standing in the hermetically sealed bottle at 45° C. for 1 month and the condition of the emulsion was visually inspected to record the results in three ratings according to the following criteria: A for absolute absence of phase separation into an oily and aqueous phases; B for slight appearance of a phase-separated layer; and C. for full phase separation into two layers.

REFERENCE EXAMPLE 1

This and following Reference Examples were undertaken for the prior art in which the formulation of the aqueous emulsion did not include the component (C).

Thus, 100 parts of the Mixture 4, 1.5 parts of stearyl trimethyl ammonium chloride and 2.5 parts of deionized water were introduced into the emulsifier machine and the mixture was agitated and emulsified by simultaneously rotating the anchor-blade stirrer and the disk stirrer at 40 rpm and at 1500 rpm, respectively, to effect phase inversion from the initially formed water-in-oil emulsion into an oil-in-water emulsion. The result, however, was that the emulsion was partly destroyed during this agitation after phase inversion so that no stable aqueous emulsion could be obtained at all.

REFERENCE EXAMPLE 2

The procedure was just the same as in Reference Example 1 described above excepting for the replacement of the Mixture 4 with the same amount of a dimethyl polysiloxane oil having a viscosity of 10,000 mm$^2$/s (KF 96H, a product by Shin-Etsu Chemical Co.) free from any high-polymeric organopolysiloxane molecular species. The oil-in-water emulsion formed by phase inversion was diluted by adding an aqueous solution of 5.5 parts of stearyl trimethyl ammonium chloride dissolved in 58.0 parts of water. The result was that, although an aqueous emulsion having an average diameter of the droplets of 25.0 $\mu$m as determined by a Coulter Counter (Model TA, manufactured by Coulter Electronics Co.) was obtained, the stability of this emulsion was rated C.

REFERENCE EXAMPLE 3

The procedure was just the same as in Reference Example 2 described above excepting for the replacement of the dimethyl silicone oil with the same amount of the Mixture 4 and of stearyl trimethyl ammonium chloride with the same amount of cetyl trimethyl ammonium chloride in the starting mixture and in the diluting solution. The result was that, although an aqueous emulsion having an average diameter of the droplets of 12.5 $\mu$m was obtained, the stability of this emulsion was rated B.

REFERENCE EXAMPLE 4

The procedure was just the same as in Reference Example 1 described above excepting for the replacement of stearyl trimethyl ammonium chloride with the same amount of behenyl trimethyl ammonium chloride. The result was that no stable aqueous oil-in-water emulsion could be obtained as in Reference Example 1.

REFERENCE EXAMPLE 5

The procedure was just the same as in Reference Example 2 described above excepting for the replacement of stearyl trimethyl ammonium chloride with the same amount of behenyl trimethyl ammonium chloride. The result was that, although an aqueous emulsion having an average diameter of the droplets of 45.0 $\mu$m was obtained, the stability of this emulsion was rated C.

As is understood from the results of the above described Reference Examples, an oil-in-water aqueous emulsion can hardly be obtained from the Mixture 4 containing a high-polymeric organopolyiloxane and the ordinary dimethyl silicone oil by using stearyl trimethyl ammonium chloride or behenyl trimethyl ammonium chloride while the same Mixture 4 can be emulsified into an oil-in-water emulsion by using cetyl trimethyl ammonium chloride although the stability of the thus obtained emulsion is not satisfactory. This fact means that a sufficient emulsifying power of the long-chain alkyl-containing quaternary ammonium salt cannot be accomplished in the prior art without being accompanied by an increase in the irritativeness to the human skin as in the cetyl, i.e. $C_{16}$ alkyl, trimethyl ammonium chloride.

EXAMPLE 1

An oil-in-water aqueous emulsion was prepared in about the same manner as in the Reference Examples from the starting ingredients including 100 parts of the Mixture 1, 1.5 parts of stearyl trimethyl ammonium chloride, 0.8 part of PESx-1 and 3.0 parts of water to effect phase inversion from a water-in-oil emulsion into an oil-in-water emulsion followed by continued agitation for up to 4 hours and then by dilution with addition of an aqueous solution of 5.0 parts of stearyl trimethyl ammonium chloride in 32.0 parts of water. Small portions of samples were taken periodically from the emulsion under continued agitation after phase inversion but before dilution and the average diameter of the droplets in each sample was determined to give the results shown in Table 2 below. The stability of the thus obtained aqueous emulsion was rated A.

EXAMPLE 2

The experimental procedure was substantially the same as in Example 1 excepting for an additional addition of 0.3 part of glycerin to the mixture of the starting ingredients. The stability of the thus obtained aqueous emulsion was rated A. Table 2 also shows the average diameter of the dispersed droplets in the emulsion under continued agitation before dilution.

EXAMPLE 3

The experimental procedure was substantially the same as in Example 1 excepting for the replacement of 1.5 parts of stearyl trimethyl ammonium chloride with 3.0 parts of distearyl dimethyl ammonium chloride and replacement of 0.8 part of PESx-1 with 0.5 part of PESx-3 in the starting mixture and replacement of 5.0 parts of stearyl trimethyl ammonium chloride in the aqueous diluting solution with 4.0 parts of distearyl dimethyl ammonium chloride in the aqueous solution for dilution. The stability of the thus obtained aqueous emulsion was rated A. Table 2 also shows the average diameter of the dispersed droplets in the emulsion under continued agitation before dilution.

COMPARATIVE EXAMPLE 1

The experimental procedure was substantially the same as in Example 1 excepting for the replacement of PESx-1 with the same amount of glycerin in the starting mixture. The stability of the thus obtained aqueous emulsion was rated C. Table 2 also shows the average diameter of the dispersed droplets in the emulsion under continued agitation before dilution.

COMPARATIVE EXAMPLE 2

The experimental procedure was substantially the same as in Example 1 excepting for a decrease in the amount of stearyl trimethyl ammonium chloride from 1.5 parts to 0.4 part and replacement of PESx-1 with the same amount of PESx-2 in the starting mixture. The result was that the phase-inversion emulsification could not take place so that no aqueous oil-in-water emulsion could be obtained.

COMPARATIVE EXAMPLE 3

The experimental procedure was substantially the same as in Example 3 excepting for an increase in the amount of water in the starting mixture from 3.0 parts to 21.0 parts. The stability of the thus obtained aqueous emulsion was rated C. Table 2 also shows the average diameter of the dispersed droplets in the emulsion under continued agitation before dilution.

As is understood from the results of Examples 1 to 3, quite satisfactory aqueous oil-in-water emulsions can be obtained by the combined use of stearyl trimethyl ammonium chloride or distearyl dimethyl ammonium chloride with the PESx compound while, as is shown by the comparison of Example 1 and Comparative Example 1, stearyl trimethyl ammonium chloride is not replaceable with glycerin because of the too large average diameter of the dispersed droplets in the aqueous emulsion obtained to exceed 20 μm. The reason for the unsuccessful result in Comparative Example 2 is presumably the too small amount of stearyl trimethyl ammonium chloride as the emulsifying agent. Further, the reason for the instability of the emulsion in Comparative Example 3 as compared with Example 3 is presumably the excessively large amount of water in the starting mixture subjected to emulsification with phase inversion before dilution.

TABLE 2

| | | Example 1 | Example 2 | Example 3 | Comparative Example 1 | Comparative Example 3 |
|---|---|---|---|---|---|---|
| Average particle diameter, μm, after hours of agitation | 0.5 | 15.2 | 19.1 | 6.8 | 35.4 | 45.0 |
| | 1 | 8.7 | 10.3 | 3.2 | 28.6 | 43.6 |
| | 2 | 5.4 | 6.4 | — | 24.2 | 42.1 |
| | 3 | 4.2 | — | — | 21.0 | 40.3 |
| | 4 | — | — | — | 26.9 | — |

EXAMPLE 4

The experimental procedure was substantially the same as in Example 1 except that the starting mixture for emulsification was formed from 100 parts of the Mixture 2, 2.0 parts of stearyl trimethyl ammonium chloride, 2.0 parts of PESx-1 and 6.0 parts of water and the aqueous solution for dilution of the emulsion after phase inversion was prepared by dissolving 6.0 parts of stearyl trimethyl ammonium chloride in 84.0 parts of water. The stability of the thus prepared aqueous emulsion was rated A. The average diameter of the dispersed droplets in the emulsion was 14.3 μm.

EXAMPLE 5

The experimental procedure was substantially the same as in Example 4 excepting for the replacement of the Mixture 2 with the same amount of the Mixture 3 and a decrease of the amount of PESx-1 from 2.0 parts to 1.0 part in the starting mixture and a decrease in the amount of water from 84.0 parts to 65.0 parts in the diluting solution. The stability of the thus prepared aqueous emulsion was rated A. The average diameter of the dispersed droplets in the aqueous emulsion was 10.1 μm.

COMPARATIVE EXAMPLE 4

The experimental procedure was substantially the same as in Example 4 excepting for the replacement of PESx-1 with the same amount of PESx-4. Although the average diameter of the dispersed dropets in the thus obtained oil-in-water emulsion was 15.0 μm, the stability of the emulsion was rated B.

COMPARATIVE EXAMPLE 5

The experimental procedure was substantially the same as in Example 5 excepting for the replacement of PESx-1 with the same amount of PESx-5. Although the average diameter of the dispersed droplets in the thus obtained oil-in-water emulsion was 11.9 μm, the stability of the emulsion was rated C.

EXAMPLE 6

The procedure for the preparation of an oil-in-water aqueous emulsion, of which the average diameter of the dispersed droplets was 3.9 μm, was substantially the same as in the preceding Examples except that the starting mixture was prepared from 100 parts of the Mixture 1, 4.5 parts of behenyl trimethyl ammonium chloride, 3.0 parts of 1,3-butyleneglycol and 4.5 parts of water and dilution of the emulsion after phase inversion was performed with an aqueous solution of 1.5 parts of behenyl trimethyl ammonium chloride in 42.0 parts of water. The length of time after phase inversion and before dilution was 1 hour. The stability of the thus obtained aqueous emulsion after dilution was rated A.

EXAMPLE 7

The procedure for the preparation of an oil-in-water aqueous emulsion, of which the average diameter of the dispersed droplets was 12.8 μm, was substantially the same as in Example 6 except that the starting mixture was prepared from 100 parts of the Mixture 2, 8.5 parts of behenyl trimethyl ammonium chloride, 7.0 parts of 1,3-butyleneglycol and 2.5 parts of water and dilution of the emulsion was performed with 50.0 parts of pure water. The stability of the thus obtained aqueous emulsion after dilution was rated A.

EXAMPLE 8

The procedure for the preparation of an oil-in-water aqueous emulsion, of which the average diameter of the dispersed droplets was 10.5 μm, was substantially the same as in Example 6 except that the starting mixture was prepared from 100 parts of the Mixture 3, 3.0 parts of behenyl trimethyl ammonium chloride, 3.0 parts of glycerin and 3.0 parts of water and dilution of the emulsion was performed with an aqueous solution of 3.0 parts of behenyl trimethyl ammonium chloride in 40.0 parts of water. The stability of the thus obtained aqueous emulsion after dilution was rated A.

COMPARATIVE EXAMPLE 6

An attempt was made to prepare an oil-in-water aqueous emulsion by agitating, in the same emulsifier machine as used in the preceding Examples, a mixture consisting of 100 parts of the Mixture 1, 4.5 parts of behenyl trimethyl ammonium chloride, 0.5 part of 1,3-butyleneglycol and 4.5 parts of water without success because no phase inversion of the emulsion took place.

COMPARATIVE EXAMPLE 7

The procedure for the preparation of an oil-in-water aqueous emulsion, of which the average diameter of the dispersed droplets was 32.6 μm, was substantially the same as in Example 6 except that the starting mixture was prepared from 100 parts of the Mixture 2, 6.5 parts of behenyl trimethyl ammonium chloride, 27.0 parts of 1,3-butyleneglycol and 2.5 parts of water and dilution of the emulsion after phase inversion was performed with 30.0 parts of pure water. The stability of the thus obtained aqueous emulsion after dilution was rated C.

COMPARATIVE EXAMPLE 8

The procedure for the preparation of an oil-in-water aqueous emulsion, of which the average diameter of the dispersed droplets was 45.0 μm, was substantially the same as in Example 6 except that the starting mixture was prepared from 100 parts of the Mixture 3, 3.0 parts of behenyl trimethyl ammonium chloride, 3.0 parts of glycerin and 21.0 parts of water and dilution of the emulsion after phase inversion was performed with 32.0 parts of pure water. The stability of the thus obtained aqueous emulsion after dilution was rated C.

COMPARATIVE EXAMPLE 9

The attempted procedure for the preparation of an oil-in-water aqueous emulsion was substantially the same as in Example 6 except that the starting mixture was prepared from 100 parts of the Mixture 1, 7.0 parts of behenyl trimethyl ammonium chloride, 5.0 parts of a polyether-modified organotrisiloxane expressed by the formula $$Me_3Si-O-SiMe[C_3H_6O(C_2H_4O)_6Me]-O-SiMe_3,$$

in which Me is a methyl group, 0.8 part of lactic acid and 2.5 parts of water. The result was that no phase inversion of the emulsion took place so that a stable aqueous emulsion of the oil-in-water type could not be obtained.

What is claimed is:

1. An oil-in-water aqueous organopolysiloxane emulsion composition which comprises, in the form of a uniform emulsion:
(A) 100 parts by weight of an organopolysiloxane mixture having a viscosity of at least 10,000 mm²/s at 25° C. and consisting of
  (A1) from 10 to 90% by weight of a first organopolysiloxane represented by the average unit formula $$R^1{}_a SiO_{(4-a)/2},$$

in which $R^1$ is a monovalent hydrocarbon group having 1 to 20 carbon atoms and the subscript a is a positive number in the range from 1.8 to 2.2, and having a viscosity of at least 1,000,000 mm²/s at 25° C., and
  (A2) from 90 to 10% by weight of a second organopolysiloxane represented by the average unit formula $$R^2{}_b SiO_{(4-b)/2},$$

in which $R^2$ is a monovalent hydrocarbon group having 1 to 20 carbon atoms and the subscript b is a positive number in the range from 1.8 to 2.2, and having a viscosity in the range from 2 to 1000 mm²/s at 25° C. or a liquid hydrocarbon compound having a boiling point under normal pressure in the range from 60 to 200° C.;
(B) from 0.5 to 20 parts by weight of a cationic surface active agent which is a quaternary ammonium halide represented by the general formula $$[R^3{}_n R^4{}_{4-n} N]^+ X^-,$$

in which $R^3$ is an alkyl or alkenyl group having 18 or 22 carbon atoms, $R^4$ is an alkyl group having 1 to 5 carbon atoms or a benzyl group, $X^-$ is a halogen ion and the subscript n is a positive integer not exceeding 4, the amount thereof being at least 1 part by weight when $R^3$ has 22 carbon atoms;
(C) from 0.05 to 20 parts by weight of an activity-promoting agent selected from the group consisting of
  (C1) when the group $R^3$ in the component (B) has 18 carbon atoms, polyoxyalkylene-modified organopolysiloxanes represented by the average unit formula $$R^5{}_c R^6{}_d SiO_{(4-c-d)/2},$$

in which $R^5$ is a monovalent hydrocarbon group having 1 to 20 carbon atoms, $R^6$ is a monovalent polyoxyalkylene-substituted alkyl group represented by the general formula $$-(C_eH_{2e})O(C_2H_4O)_f(C_3H_6O)_g R^7,$$

$R^7$ being a hydrogen atom or an alkyl or acyl group having 1 to 20 carbon atoms, the subscript e being a positive integer in the range from 2 to 15, the subscript f being a positive integer in the range from 3 to 200 and the subscript g being 0 or a positive integer not exceeding 100, the subscript c is a number in the range from 1.0 to 2.5 and the subscript d is a number in the range from 0.005 to 1.2 with the proviso that c+d is in the range from 1.8 to 3.0, and
  (C2) when the group $R^3$ in the component (B) has 22 carbon atoms, polyhydric alcohols, the amount thereof being at least 1 part by weight when the activity promoting agent is a polyhydric alcohol; and
(D) from 10 to 300 parts by weight of water.

2. The oil-in-water aqueous organopolysiloxane emulsion composition as claimed in claim 1 in which the component (A2) to form the component (A) with the component (A1) is the second organopolysiloxane.

3. The oil-in-water aqueous organopolysiloxane emulsion composition as claimed in claim 1 in which at least 50% by moles of the groups denoted by $R^1$ in the component (A1) are methyl groups, the rest, if any, being phenyl groups or amino-substituted alkyl groups.

4. The oil-in-water aqueous organopolysiloxane emulsion composition as claimed in claim 1 in which the first organopolysiloxane as the component (A1) has a viscosity of at least 10,000,000 mm²/s at 25° C.

5. The oil-in-water aqueous organopolysiloxane emulsion composition as claimed in claim 2 in which the second organopolysiloxane as the component (A2) has a viscosity in the range from 10 to 500 mm²/s at 25° C.

6. The oil-in-water aqueous organopolysiloxane emulsion composition as claimed in claim 2 in which the component (A) as a mixture of the first organopolysiloxane as the component (A1) and the second organopolysiloxane as the component (A2) has a viscosity of at least 100,000 mm²/s at 25° C.

7. The oil-in-water aqueous organopolysiloxane emulsion composition as claimed in claim 1 in which the group denoted by $R^3$ in the component (B) is a stearyl group or behenyl group.

8. The oil-in-water aqueous organopolysiloxane emulsion composition as claimed in claim 1 in which the group denoted by $R^4$ in the component (B) is a methyl group or benzyl group.

9. The oil-in-water aqueous organopolysiloxane emulsion composition as claimed in claim 1 in which the subscript n in the general formula representing the component (B) is 1 or 2.

10. The oil-in-water aqueous organopolysiloxane emulsion composition as claimed in claim 1 in which the halogen ion denoted by $X^-$ in the general formula representing the component (B) is a chlorine ion.

11. The oil-in-water aqueous organopolysiloxane emulsion composition as claimed in claim 1 in which the subscript c in the average unit formula representing the component (C1) is a number in the range from 1.2 to 2.3.

12. The oil-in-water aqueous organopolysiloxane emulsion composition as claimed in claim 1 in which the subscript d in the average unit formula representing the component (C1) is a number in the range from 0.01 to 1.0.

13. The oil-in-water aqueous organopolysiloxane emulsion composition as claimed in claim 1 in which the subscript e in the general formula representing the polyoxyalkylene-substituted alkyl group in the component (C1) is a positive integer in the range from 3 to 12.

14. The oil-in-water aqueous organopolysiloxane emulsion composition as claimed in claim 1 in which the polyoxyalkylene-modified organopolysiloxane as the component (C1) has a molecular weight not exceeding 3000 and an HLB value of at least 7.

15. The oil-in-water aqueous organopolysiloxane emulsion composition as claimed in claim 1 in which the polyhydric alcohol as the component (C2) is selected from the group consisting of ethyleneglycol, propyleneglycol, diethyleneglycol, 1,3-butyleneglycol, 1,4-butyleneglycol, glycerin, diglycerin, triglycerin and trimethylol propane.

16. The oil-in-water aqueous organopolysiloxane emulsion composition as claimed in claim 15 in which the polyhydric alcohol as the component (C2) is glycerin or 1,3-butyleneglycol.

17. The oil-in-water aqueous organopolysiloxane emulsion composition as claimed in claim 1 in which the amount of water as the component (D) is in the range from 20 to 100 parts by weight per 100 parts by weight of the component (A).

18. The oil-in-water aqueous organopolysiloxane emulsion composition as claimed in claim 1 in which the droplets as the dispersed phase of the oil-in-water emulsion have a particle diameter in the range from 2 to 20 $\mu$m.

19. A method for the preparation of an oil-in-water aqueous organopolysiloxane emulsion composition which comprises the successive steps of:
(a) agitating a mixture consisting of 100 parts by weight of the component (A), from 0.5 to 20 parts by weight of the component (B), from 0.05 to 20 parts by weight of the component (C), each of the components (A), (B) and (C) being defined as in claim 2 above, and from 0.5 to 20 parts by weight of water to form a water-in-oil emulsion;
(b) agitating the water-in-oil emulsion until phase inversion of the water-in-oil emulsion into an oil-in-water emulsion is effected followed by further continued agitation; and
(c) diluting the oil-in-water emulsion obtained in step (b) with addition of an additional amount of water in such an amount as to make up an overall amount of water not exceeding 300 parts by weight.

20. The method for the preparation of an oil-in-water aqueous organopolysiloxane emulsion composition as claimed in claim 19 in which the length of time for the agitation of the oil-in-water emulsion after phase inversion in step (b) is in the range from 20 minutes to 3 hours before dilution with water.

21. The method for the preparation of an oil-in-water aqueous organopolysiloxane emulsion composition as claimed in claim 19 in which the amount of the component (B) taken in step (a) is smaller than 20 parts by weight and the water additionally added in step (c) contains the component (B) dissolved therein in an amount to make up an overall amount of the component (B) not exceeding 20 parts by weight.

\* \* \* \* \*